US008300911B1

(12) United States Patent
Payne et al.

(10) Patent No.: US 8,300,911 B1
(45) Date of Patent: Oct. 30, 2012

(54) METHODS AND APPARATUS FOR MEASURING VISCERAL FAT MASS

(75) Inventors: Randall Payne, Madison, WI (US); David Ergun, Verona, WI (US); James Wear, Madison, WI (US); Wynn Wacker, Madison, WI (US); Howard Barden, Madison, WI (US)

(73) Assignee: General Electric Company, Schenectady, NY (US)

( * ) Notice: Subject to any disclaimer, the term of this patent is extended or adjusted under 35 U.S.C. 154(b) by 429 days.

(21) Appl. No.: 12/557,285

(22) Filed: Sep. 10, 2009

(51) Int. Cl.
*G06K 9/00* (2006.01)
(52) U.S. Cl. .................................. 382/128; 128/922
(58) Field of Classification Search .................. 382/100, 382/128, 129, 130, 131, 132; 128/922; 378/4–27
See application file for complete search history.

(56) References Cited

U.S. PATENT DOCUMENTS

| 6,081,582 | A | 6/2000 | Mazess et al. | |
|---|---|---|---|---|
| 6,088,615 | A | 7/2000 | Masuo | |
| 6,198,797 | B1 * | 3/2001 | Majima et al. | 378/98 |
| 6,752,760 | B2 * | 6/2004 | Kouou | 600/301 |
| 6,850,797 | B2 | 2/2005 | Kawanishi et al. | |
| 6,978,170 | B1 * | 12/2005 | Onda et al. | 600/547 |
| 7,065,235 | B2 | 6/2006 | Dewaele | |
| 7,089,052 | B2 * | 8/2006 | Kodama et al. | 600/547 |
| 7,196,332 | B2 | 3/2007 | Wear et al. | |
| 7,292,721 | B2 * | 11/2007 | Arnold | 382/131 |
| 7,421,104 | B2 | 9/2008 | Hsieh et al. | |
| 7,725,153 | B2 * | 5/2010 | Kelly et al. | 600/407 |
| 2003/0065264 | A1 | 4/2003 | Tsoref et al. | |
| 2006/0074288 | A1 * | 4/2006 | Kelly et al. | 600/407 |
| 2008/0021349 | A1 | 1/2008 | Sakai et al. | |
| 2008/0146961 | A1 | 6/2008 | Okura et al. | |
| 2010/0234719 | A1 * | 9/2010 | Kelly et al. | 600/407 |
| 2010/0278405 | A1 * | 11/2010 | Kakadiaris et al. | 382/131 |

OTHER PUBLICATIONS

Cao et al., Digital Hand Atlas and Web-Based Bone Age Assessment: System Design and Implementation, Computerized Medical Imaging and Graphics 24 (2000) 297-307.

Gertych et al., Bone Age Assessment of Children Using a Digital Hand Atlas, Computerized Medical Imaging and Graphics 31 (2007) 322-331.

Bertin et al., Measurement of Visceral Adipose Tissue by DXA Combined With Anthropometry in Obese Humans, International Journal of Obesity (2000) 24, 263-270.

(Continued)

*Primary Examiner* — Anand Bhatnagar (57) ABSTRACT

Methods and apparatus for measuring visceral fat mass are provided. One method includes acquiring dual-energy two-dimensional (2D) scan information from a dual-energy x-ray scan of a body and generating a dual-energy image of the body using the 2D scan information. The method further includes identifying a region of interest using the dual-energy image and determining a subcutaneous fat mass for each of a plurality of sections of the region of interest. The method also includes determining a visceral fat mass for the region of interest based on the determined subcutaneous fat mass for each of the plurality of sections.

14 Claims, 7 Drawing Sheets

OTHER PUBLICATIONS

Sabharwal et al., Computed Radiographic Measurement of Limb-Length Discrepancy. Full Length Standing Anteroposterior Radiograph Compared With Scanogram, The Journal of Bone & Joint Surgery (2006)88, 2243-2251.

Pietka et al., Computer-Assisted Bone Age Asessment: Graphical User Interface for Image Processing and Comparison, Journal of Digital Imaging vol. 17 No. 3 (2004) 175-188.

Pietka et al., Integration of Computer Assisted Bone Age Assessment With Clinical PACS, Computerized Medical Imaging and Graphics 27 (2003) 217-228.

Pietka, Computer-Assisted Bone Age Assessment Based on Features Automatically Extracted From a Hand Radiograph, Computerized Medical Imaging and Graphics vol. 19 No. 3 (1995) 251-259.

* cited by examiner

METHODS AND APPARATUS FOR MEASURING VISCERAL FAT MASS

BACKGROUND OF THE INVENTION

The subject matter disclosed herein relates generally to medical diagnostic imaging systems, and more particularly, to diagnostic imaging systems that acquire bone and tissue information.

Characteristics of an individual, such as body weight, fat mass, height, girth, gender, age, etc. are clinical descriptors useful by physicians to predict certain health risks that may increase or decrease mortality and morbidity risk. For example, the amount or type of abdominal fat, such as subcutaneous adipose tissue (SAT) and visceral adipose tissue (VAT) are associated with, and useful predictors of, an adverse metabolic risk profile and certain diseases, such as coronary heart disease and diabetes. In addition, measuring visceral fat, for example, can relate to metabolic syndrome—i.e., a combination of medical problems that can increase the risk of heart disease and/or diabetes. People suffering from metabolic syndrome can have some or all of the following: high blood glucose, high blood pressure, abdominal obesity, low HDL elevated cholesterol, and/or high triglycerides.

Conventional methods for measuring VAT are mostly performed using anthropomorphic gauges, bioimpedance gauges, weight scales, etc. These devices often are not capable of providing accurate measurements because the actual fat content is not being measured, certain assumptions/estimates are made during the calculation process, and/or the devices are not exactly calibrated. Also, reproducibility may be difficult, leading to inaccurate comparisons between examinations.

Imaging systems have also been used to measure VAT content. However, examination with these systems are often costly and can expose a patient to high levels of ionizing radiation, for example, when using a computed-tomography (CT) system. Additionally, these systems are not always available for clinical use and may have long scan times. Moreover, certain measurements are inaccurate in larger subjects.

Conventional methods for determining VAT often also use simple models to approximate the abdominal cavity from an estimate of subcutaneous thickness measurements. These methods can often fail to accurately estimate the SAT, thereby resulting in an inaccurate estimate of the VAT.

BRIEF DESCRIPTION OF THE INVENTION

In accordance with one embodiment, a method for determining visceral fat of a body is provided. The method includes acquiring dual-energy two-dimensional (2D) scan information from a dual-energy x-ray scan of a body and generating a dual-energy image of the body using the 2D scan information. The method further includes identifying a region of interest using the dual-energy image and determining a subcutaneous fat mass for each of a plurality of sections of the region of interest. The method also includes determining a visceral fat mass for the region of interest based on the determined subcutaneous fat mass for each of the plurality of sections.

In accordance with another embodiment, a method for determining visceral fat mass of an abdomen region of a body is provided. The method includes acquiring body composition information using a planar dual-energy x-ray imaging system and segmenting visceral fat in the abdomen region using the acquired body composition information to determine the visceral fat mass.

In accordance with yet another embodiment, a diagnostic imaging system is provided that includes a dual-energy x-ray bone densitometer configured to acquire body composition information from a dual-energy imaging scan of a subject. The diagnostic imaging system further includes a body fat measurement module configured to segment visceral fat in an abdomen region of the subject to determine an amount of visceral fat mass in the abdomen region using the body composition information.

DETAILED DESCRIPTION OF THE INVENTION

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. One or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Exemplary embodiments of dual-energy x-ray systems and methods for scanning bodies to obtain or determine bone and tissue information, particularly soft tissue information, such as visceral adipose tissue information, are described in detail below. Various embodiments calculate or estimate abdominal visceral fat mass using dual x-ray absorptiometry (DXA). At least one technical effect of the various embodiments of the systems and methods described herein is to determine visceral fat mass in the abdomen using a soft tissue composition profile acquired from a DXA scan. Different methods or models are used to measure the fat mass in different regions.

Figure 1:
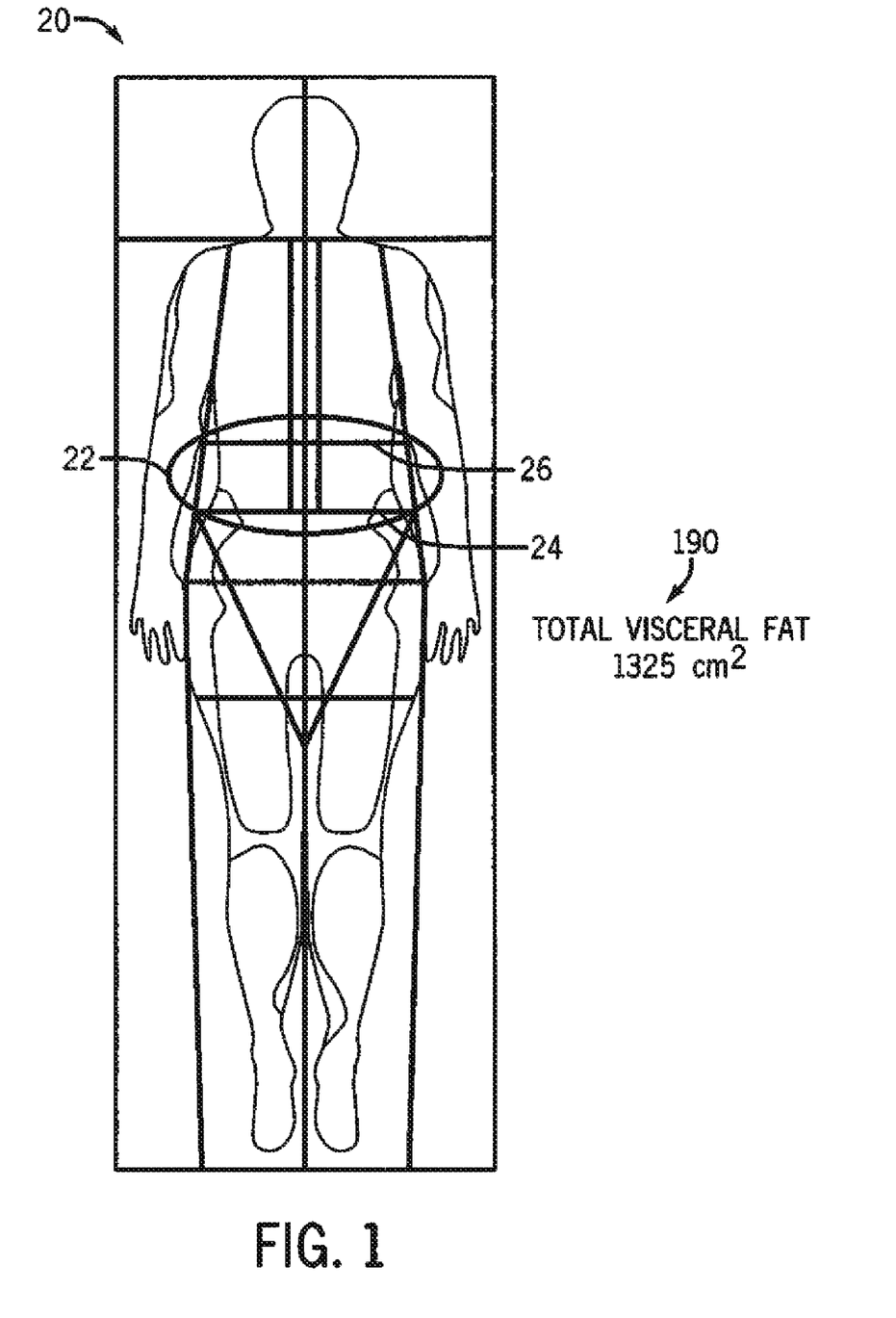
FIG. 1 is a dual-energy x-ray image identifying an abdomen region of interest and used to determine an abdominal visceral fat mass in accordance with various embodiments.

FIG. 1 is an image of a body (e.g., a patient's body), and more particularly, a full body dual-energy image 20 that may be generated from a scan of the entire body using a dual-energy x-ray system. The illustrated dual-energy image 20 is a dual-energy tissue image. The image 20 is generated from a full body scan, which in some embodiments includes acquiring all bone and tissue information during a single scan, for example, a single imaging pass or operation. The total body scan may be acquired using different dual-energy imaging systems, for example, the Lunar iDXA imaging system available from GE Healthcare or other bone densitometer systems. The Lunar iDXA imaging system generally has no parallax in the transverse scanning direction. An embodiment of a dual-energy x-ray imaging system is described in more detail below in connection with FIG. 2.

The image 20 allows for the identification of different portions or regions of the imaged body. For example, an android region 22 of the imaged body can be determined using the image 20. For example, based on bone and tissue information of the imaged body, the android region 22 can be identified and the visceral fat mass thereof estimated or calculated using the acquired bone and tissue information. A lower boundary 24 and an upper boundary 26 of the android region 22 may be determined and identified using information acquired during the dual-energy x-ray scan, including the image 20 and tissue information, including fat and lean tissue information. The android region 22 generally corresponds to the abdomen of a subject.

In general, the image 20 formed from the dual-energy x-ray imaging system is a 2D image of a three-dimensional (3D) body. In particular, the image 20 is an anterior-posterior (AP) image of a body acquired using a dual-energy x-ray imaging system. The image may also be referred to as a posterior-anterior (PA) image of the body. The dual-energy x-ray system can be used to acquire both bone and tissue information (particularly soft tissue information) from one or more projection measurements of x-ray attenuation at two different x-ray energy ranges. For example, when a patient is lying down on a table between an x-ray source below the patient and an x-ray detector above the patient (or vice versa), the detector can obtain information for a dual-energy x-ray absorptiometry (DEXA or DXA) AP view of the composition of the body, including tissue, as well as the spine, bones or a portion thereof as a result of the passage of x-rays at two different energy levels through the patient.

Figure 2:
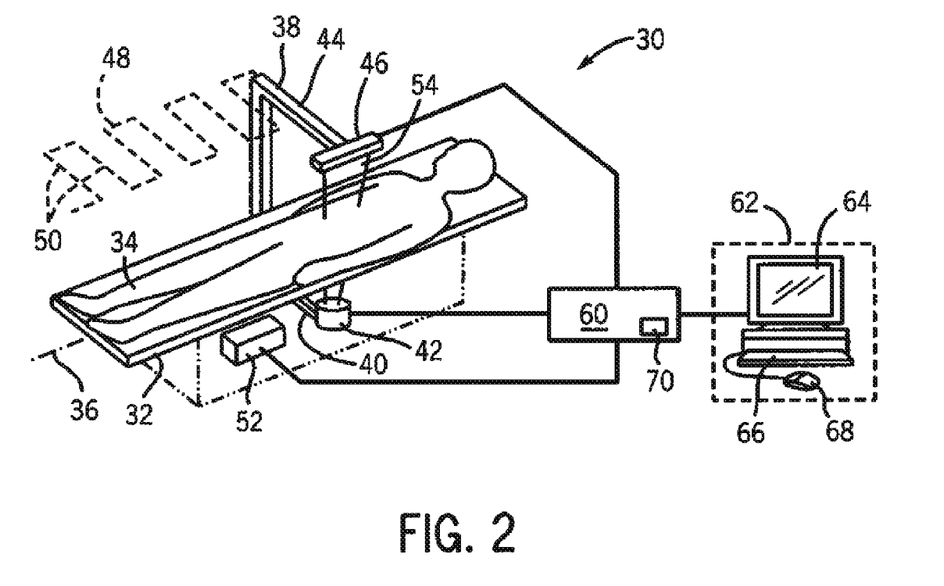
FIG. 2 is diagram illustrating a dual-energy x-ray imaging system formed in accordance with various embodiments illustrating a scan to acquire the image of FIG. 1.

FIG. 2 is a block diagram of an exemplary dual-energy x-ray system, illustrated as a dual x-ray absorptiometry (DEXA or DXA) system 30, which is also referred to as dual-energy bone densitometer system capable of performing bone densitometry. The system 30 constructed in accordance with various embodiments is configured to provide for measurement of at least soft tissue composition (including tissue thickness), an area of a bone, a length of a bone, a bone mineral content (BMC), and a bone mineral density (BMD). The BMD is calculated by dividing the BMC by the area of the bone. During operation, two x-ray beams having different energy levels are utilized to scan an object, for example, to scan a body of a human subject (e.g., a patient) to image the body of the human subject. The acquired image(s), including tissue and bone information from the imaged body, particularly determined tissue composition and thickness information, is used to calculate a visceral fat mass of the abdomen region. The images may be generated in part from determined tissue information and bone density information acquired during a dual-energy x-ray scan.

The system 30 includes a patient table 32 providing a horizontal surface for supporting a subject, for example, a patient 34 in a supine or lateral position along a longitudinal axis 36. The system 30 also includes a support member, for example, a C-arm 38. The C-arm 38 has a lower end 40 that is positioned beneath the patient table 32 to support an x-ray source 42. The C-arm 38 has an upper end 44 that is positioned above the patient table 32 supporting an x-ray detector 46. However, it should be noted that the position of the x-ray source 42 and x-ray detector 46 may be reversed. The x-ray detector 46 may be fabricated, for example, as a multi-element cadmium-zinc-telluride (CZT) detector providing for energy discrimination. The x-ray source 42 and the x-ray detector 46 may be moved in a raster pattern 48 so as to trace a series of transverse scans 50 of the patient 34 during which dual-energy x-ray data is collected by the x-ray detector 46. The raster motion is produced by actuators (not shown) under control of a translation controller 52. During operation, the x-ray source 42 produces a fan beam 54 having a plane that is parallel to the longitudinal axis 36. However, in some embodiments, the fan beam 54 may be provided perpendicular to the longitudinal axis 36. The raster pattern 48 is adjusted in some embodiments such that there is some overlap (e.g., slight overlap of 10 percent) between successive scan lines of the fan beam 54.

The x-ray source 42, the x-ray detector 46, and the translation controller 52 communicate with, and are under the control of, a computer 60 which may include both dedicated circuitry and one or more processors having the ability to execute a stored program. In the exemplary embodiment, the computer 60 also includes a body fat measurement module 70. The module 70 utilizes the scan data or the scanned image, and in particular, the acquired tissue and bone information to determine an amount of visceral fat, and more particularly, abdominal visceral fat of a scanned body of the patient 34. During operation, the module 70 directs the dual-energy imaging system 30 to acquire a scan of a portion of the body or a full body (or total body scan), from which tissue information as well as certain bones may be identified. The locations of bone landmarks may be determined automatically, manually or semi-automatically, for example, with an operator adjusting automatically generated landmarks and used to identify regions of the imaged body.

The module 70 then utilizes the scan data or scan image(s), including the acquired tissue information (particularly soft tissue information) and bone information to determine the visceral fat mass in one or more regions of the patient. In various embodiments, using tissue and bone information or measurements in combination with different methods or models, abdominal visceral fat is determined as described in more detail below. It should be noted that different landmarks may be used to identify one or more regions of interest for which the visceral fat mass is to be determined. It also should be noted that different methods or models may be used to determine the visceral fat mass in different sections of the 2D planar scan from the imaging system 30. It further should be noted that although the various embodiments are described in connection with a dual-energy x-ray imaging system, the various embodiments are not limited to a dual-energy x-ray imaging system or a particular configuration thereof.

Referring again to FIG. 2, the computer 60 communicates with a terminal, such as a workstation 62 including a display 64, a keyboard 66, and a cursor control device such as a mouse 68 allowing for operator input and the output of text and images to the operator. In some embodiments, the computer 60 is located remotely from the workstation 62. Optionally, the computer 60 may form a portion of the workstation 62. The computer is adapted to perform one or more processing operations. The acquired tissue and bone information, for example, image, density and thickness information may be processed and displayed in real-time during a scanning session as the data is received. Additionally or alternatively, the data may be stored temporarily in a memory device on the computer 60 during a scanning session and then processed and displayed in an off-line operation. The information may also be stored in a long-term storage device (e.g., hard-drive or server) for later access, such as during a follow-up scan of the same patient, allowing monitoring changes in the visceral fat mass of the abdomen. The display 64 includes one or more monitors that present patient information, including the scanned image, which may include presenting tissue and bone information to the operator for review, diagnosis and/or analysis. The displayed images may be modified and the display settings of the display 64 also manually adjusted using the keyboard 66, the mouse 68, or a touch screen icon on the display itself.

During operation, the system 30 is configured to operate in either a dual-energy x-ray mode or a single energy x-ray mode. In the single energy mode, the x-ray source 42 emits x-rays at a narrow band of energies of a few keV and in the diagnostic imaging range of approximately 20-150 keV. In the dual-energy mode, the x-ray source 42 emits radiation at two or more bands of energy emitted simultaneously or in rapid succession. The x-ray source 42 may also be configured to emit a single broadband energy of more than a few keV over the diagnostic imaging range. The system 30 may be switched between the dual-energy mode and the single energy mode by increasing or decreasing the x-ray source 42 voltage and/or current. The system 30 may also be switched between the dual-energy mode and the single energy mode by removing or adding a K-edge filter. It should be noted that the x-ray source 42 may emit x-rays at different energies or ranges of energies.

The x-ray source 42 may be configured to output a fan beam of x-rays 54 as shown in FIG. 2. The x-ray source 42 may also be configured to output a pencil beam of x-rays (not shown), a cone beam of x-rays, or other configurations. In some embodiments, the module 70 controls the system 30 to operate in the single energy mode or dual-energy mode to acquire tissue and bone information to determine the visceral fat mass of one or more portions or regions of a scanned body. The dual-energy mode allows the acquisition of both tissue information and skeletal bone information, for example, soft tissue information, such as fat density or fat thickness information. Accordingly, the dual-energy mode allows for both soft tissue and skeletal imaging of the patient 34 using attenuation information from the different energy levels. It should be noted that in the single energy mode, higher resolution images also may be generated.

Various embodiments provide for calculating or estimating the visceral fat mass of one or more different portions or regions of a scanned body. The tissue and bone information used for calculating the visceral fat mass is acquired in the various embodiments using a one or more dual-energy scans. For example, region specific scans may be performed where only a portion or region of the patient 34 (e.g., abdominal region) of interest is scanned for use in calculating the visceral fat mass. In other embodiments, a full body or total body scanned is performed.

Figure 3:
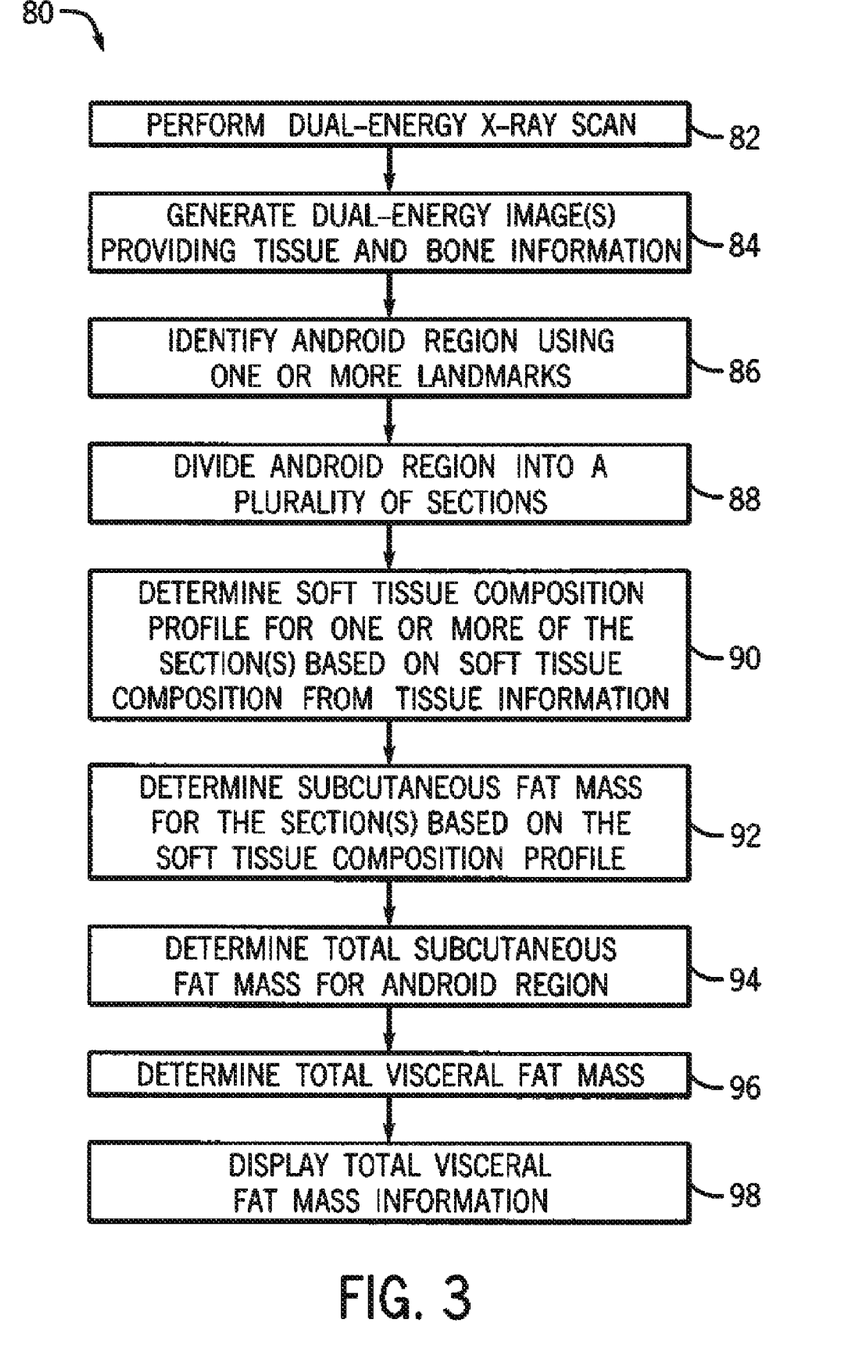
FIG. 3 is a flowchart of a method for calculating visceral fat mass in accordance with various embodiments.

A method 80 for calculating visceral fat mass is shown in FIG. 3. It should be noted that although the method 80 and the various embodiments are described in connection with calculating the visceral fat mass for a particular body volume or body part, for example, for the android region or abdomen, the method 80 and the various embodiments may be used to calculate the visceral fat mass for any portion of the imaged body. In some embodiments, and as described in more detail below, the method 80 uses a planar dual-energy x-ray imaging system to segment visceral fat in the abdomen.

The method 80 includes performing at 82 a dual-energy x-ray scan of an object, such as a patient or a portion of a patient. The patient in some embodiments lies supine on a table of a dual-energy x-ray imaging system, such as a bone densitometer system. However, in other embodiments, the patient may be imaged with a bone densitometer system wherein the patient is imaged in a standing position or other position.

The dual-energy x-ray scan may be a rectilinear scan of the a portion of the patient of the entire patient body, which may be performed in a raster-type scanning sequence as described in more detail herein. During the dual-energy x-ray scan an image of a portion of or the entire patient may be acquired, which includes tissue information, from which soft tissue composition may be determined, and bone information relating to the bones in the skeleton. For example, a dual-energy detector receives a beam after the beam has passed through the patient to generate electrical signals indicating the attenuation of the beam by the patient within distinct first and second energy ranges. Images such as a bone density images, tissue images, particularly soft tissue images, or a combination thereof are produced based on the attenuation of the x-ray radiation in the first and second energy ranges. Thus, the dual-energy system allows not only the formation of a radiographic attenuation image, but also the mathematical analysis of the composition of the attenuating material by dual-energy techniques. For example, dual-energy techniques may be used that quantitatively compare the attenuation of radiation at two energies to distinguish between bone and soft tissue, as well as to distinguish between different types of tissue, for example, different types of fat as described in more detail herein. In various embodiments, the dual-energy scan acquires dual-energy 2D (planar) scan information.

It should be noted that a full body or total body scan of the entire body may be performed as a single scanning operation, which may be a low dose mode scan. In some embodiments, instead of a full body or total body scan, individual smaller scans of a region of interest, for example, the android region, may be performed in single sweep or rectilinear scans.

Referring again to the method 80, thereafter one or more dual-energy images are generated at 84 with each containing at least one of bone information, for example, bone image information and bone content information, as well as soft tissue information, for example, fat content or fat mass or thickness information, thereby providing soft tissue composition information. For example, an image 20 as shown in FIG. 1 may be generated from a scan of the entire body and includes soft tissue information. Bone and soft tissue information may be separately identified, for example, by setting different attenuation thresholds, such as an attenuation range that defines bone, soft tissue and air. The settings may be predetermined, determined by a user or adjusted by a user. Alternatively, one or more dual-energy region images may be generated, which are smaller than the full body dual-energy image 20.

Figure 4:
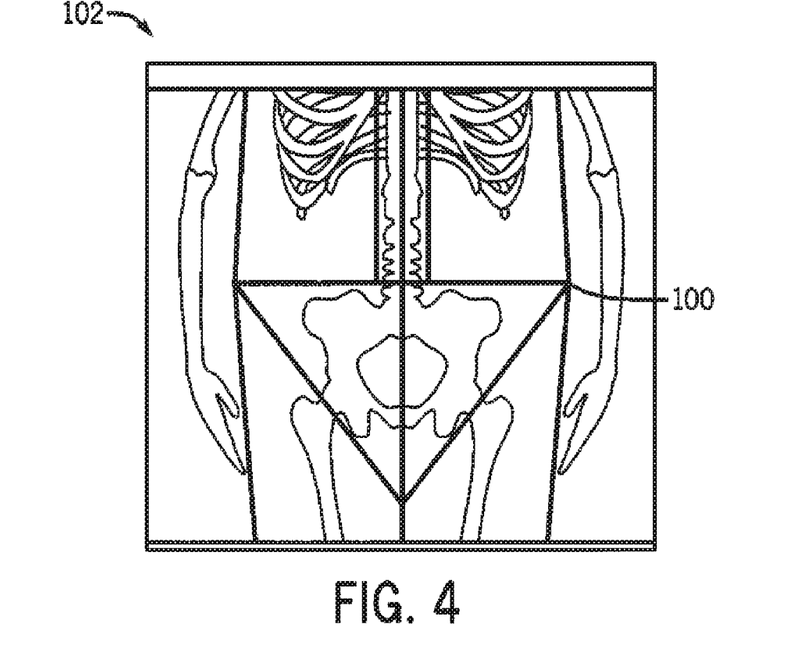
FIG. 4 is a dual-energy bone image of a portion of an imaged subject illustrating a landmark used to identify an abdomen in accordance with various embodiments.
Figure 5:
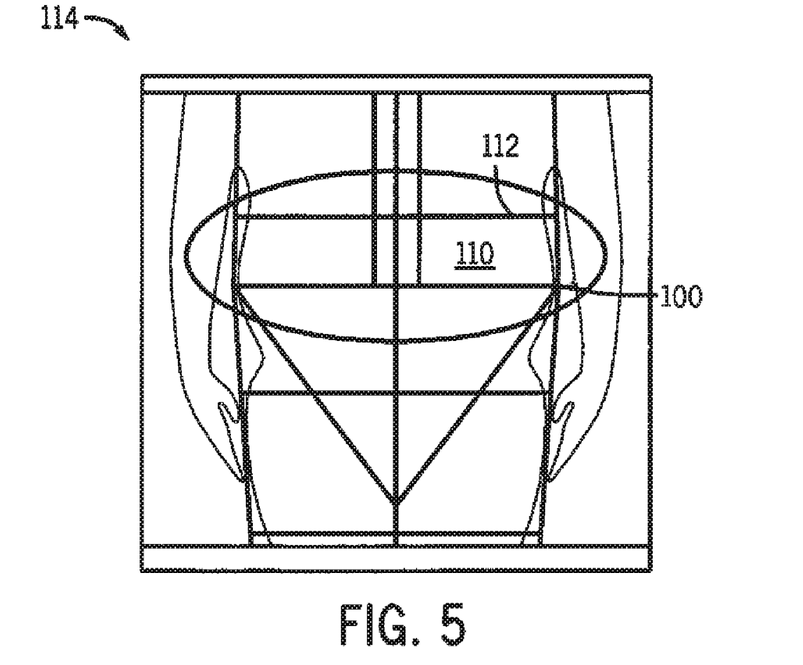
FIG. 5 is a dual-energy tissue image identifying an abdomen region of an imaged subject in accordance with various embodiments.

Using one or more dual-energy image(s), for example, as shown in FIGS. 4 and 5, a region of interest, which in various embodiments is the android region or abdomen, is identified using one or more landmarks at 86. For example, landmarks are identified that allow for locating one or more scan lines that encompass a region of interest, such as the android region. It should be noted that the dual-energy image is composed of data of a variety of scan lines associated with each of the rays detected by the dual-energy system x-ray detector. Bone density and soft tissue information may be determined from the information corresponding to each of the scan lines, for example, attenuation information corresponding thereto. The measurements of each scan line produce measurements at a set of discrete pixels that represent a bone and soft tissue density along the ray line of that measurement. The bone and tissue density may be mapped to a gray scale to present images to the operator.

The landmarks may correspond to different regions of interest and may be determined automatically, manually or semi-automatically. In some embodiments, landmarks are identified that are used to determine imaged portions (e.g., one or more scan lines) that correspond to an android region. It should be noted that the landmarks are not limited to a particular kind or type of landmark, for example, a bone, but may be an area defined by soft tissue or other body elements. As an example, in embodiments where an android region is to be identified, the various embodiments may identify the top of the iliac crest of the pelvis, identified in the image 102 of FIG. 4 by the line 100, as determined from an imaged pelvis bone from a dual-energy scan as shown. For example, the iliac crest may be determined as the superior border of the wing of the ilium and the superolateral margin of the greater pelvis. In general, the iliac crest stretches posteriorly from the anterior superior iliac spine (ASIS) to the posterior superior iliac spine (PSIS).

The identification of the iliac crest may be performed in different ways. For example, the iliac crest may be determined manually by a user viewing a full body dual-energy image and placing a line (e.g., using a mouse) at the region of the image where the iliac crest is observed. It should be noted that the line may be defined by two endpoints or may be generated and then increased or decreased in length as needed, as well as moved or adjusted. Additionally, the line may encompass one or more scan lines or only one scan line. The iliac crest also may be identified automatically using any method, for example, a template matching method or by searching for the widest bone structure in the hip region and identifying the top of that bone structure. It should be noted that when the automatic identification method is used, a user may still adjust the identified location of the iliac crest, for example, by moving an automatically generated line. It also should be noted that any method may be used to determine the iliac crest and the identification thereof is not limited to the methods described above.

The android region is then determined from the top of the iliac crest. For example, the android region 110 as shown in the image 114 of FIG. 5 is defined between the line 100 identifying the top of the iliac crest and the line 112, which is defined by a predetermined distance from the line 100. For example, the distance of the line 112 from the line 100 in some embodiments is defined as twenty percent of the distance from the top of the iliac crest (the top of the pelvis) to the base of the skull. It should be noted that this distance may be determined from bone information from a full body scan using a pixel counting method between the two landmarks. In the pixel counting method, the distance from the top of the iliac crest to the base of the skull is measured using a pixel count (as each pixel in the full body dual-energy image has a known size in the vertical and horizontal direction). In other embodiments, the line 112 is defined by a predetermined distance from the line 100, for example, ten centimeters, fifteen centimeters, etc. It should be noted that the distance between the line 100 and the line 110 may also be based in part on certain characteristics of the patient, for example, patient height, age, etc. The android region 110 generally defines an abdominal region of interest (ROI) for which measurement of visceral fat mass is accordance with various embodiments is performed.

Figure 6:
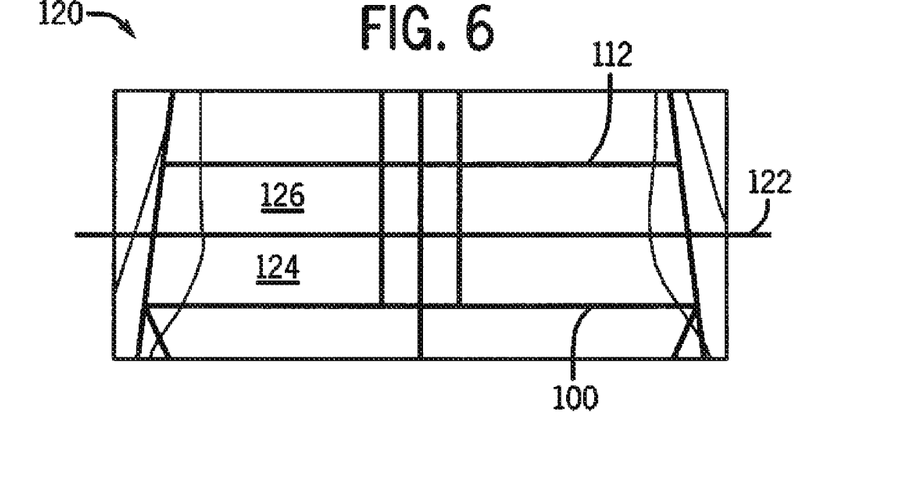
FIG. 6 is a dual-energy tissue image of an abdomen region of an imaged subject illustrating different sections used to determine an abdominal visceral fat mass in accordance with various embodiments.

Referring again to the method 80 shown in FIG. 3, once the android region 110 (see, e.g., FIG. 5) is identified, the android region 110 is divided into a plurality of sections at 88. For example, as shown in the image 120 of FIG. 6, the android region 110 is divided by a line 122 (which may be user defined or automatically defined) into two halves, namely divided into equal fifty percent sections, illustrated as sections 124 and 126. Accordingly, the section 124 defines an inferior area and the section 126 defines a superior area. It should be noted that the android region 110 may be divided into more than two sections. Additionally, the sections into which the android region 110 is divided may be equal in size or unequal in size.

Figure 7:
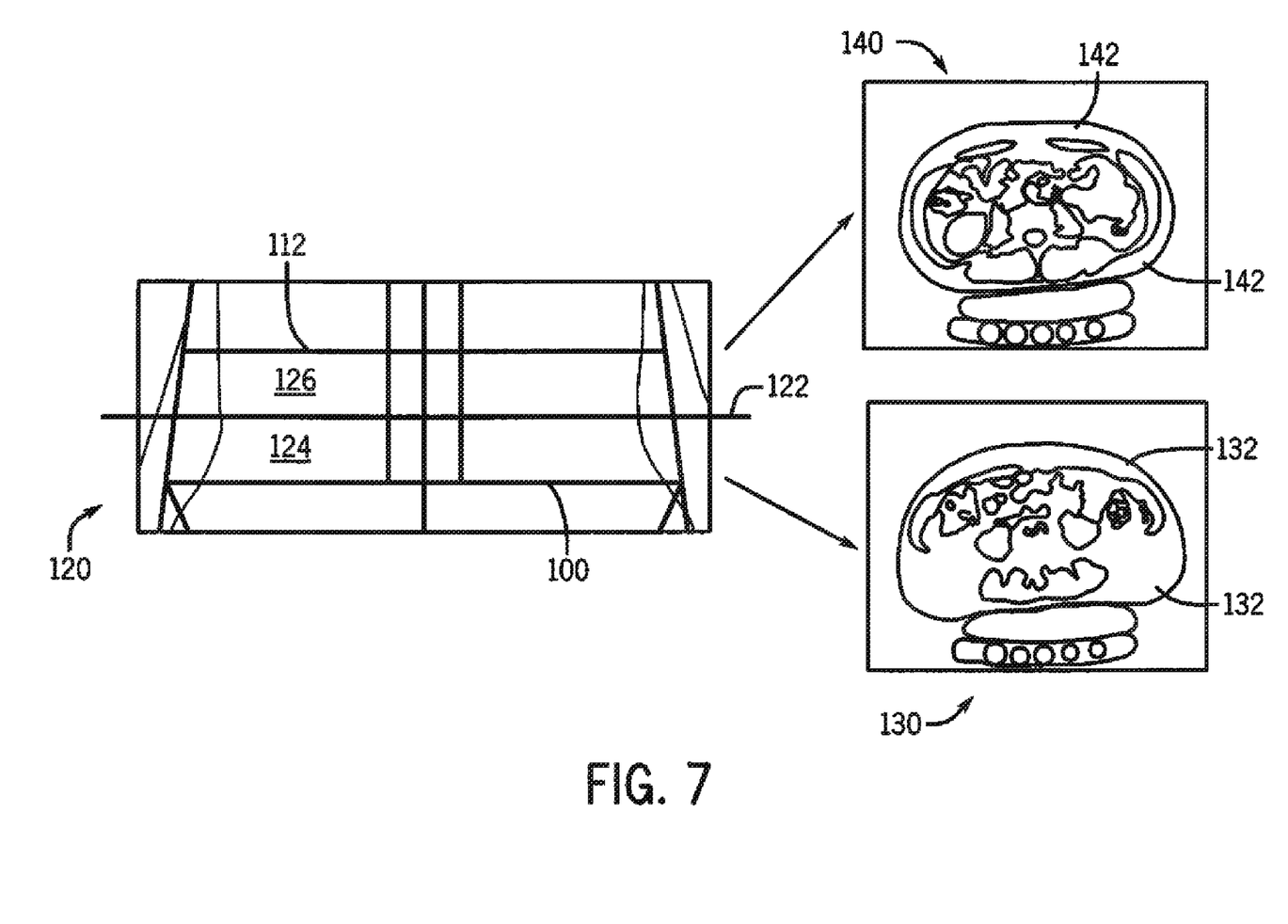
FIG. 7 is a diagram showing images illustrating different body compositions at different sections of the abdomen.

Thereafter, a soft tissue composition profile is determined at 90 for one or more of the sections 124 or 126 based on acquired soft tissue composition information, for example, soft tissue information from the imaged body. The body composition at different sections of the abdomen, including the soft tissue profile for each of the sections is different as illustrated FIG. 7. In particular, the images 130 and 140 illustrate body content or composition at each of the sections 124 and 126, respectively, of a human body and are shown in FIG. 7 merely to illustrate the body composition at the different regions. It should be noted that these cross-sectional images were not generated by a dual-energy x-ray imaging system, which as described above generates one or more 2D planar images of a body in the AP or PA direction. However, using the dual-energy x-ray imaging system, bone information or images can be displayed and tissue or fat thickness and composition determined as described above. The images 130 and 140 illustrate that the amount of fat, for example, the amount of soft adipose tissue 132 and 142, respectively, is different in each of the sections 124 and 126. As can be seen, the soft adipose tissue 132 in the section 124 is higher than the soft adipose tissue 142 in the section 126 due to the buttocks.

Figure 8:
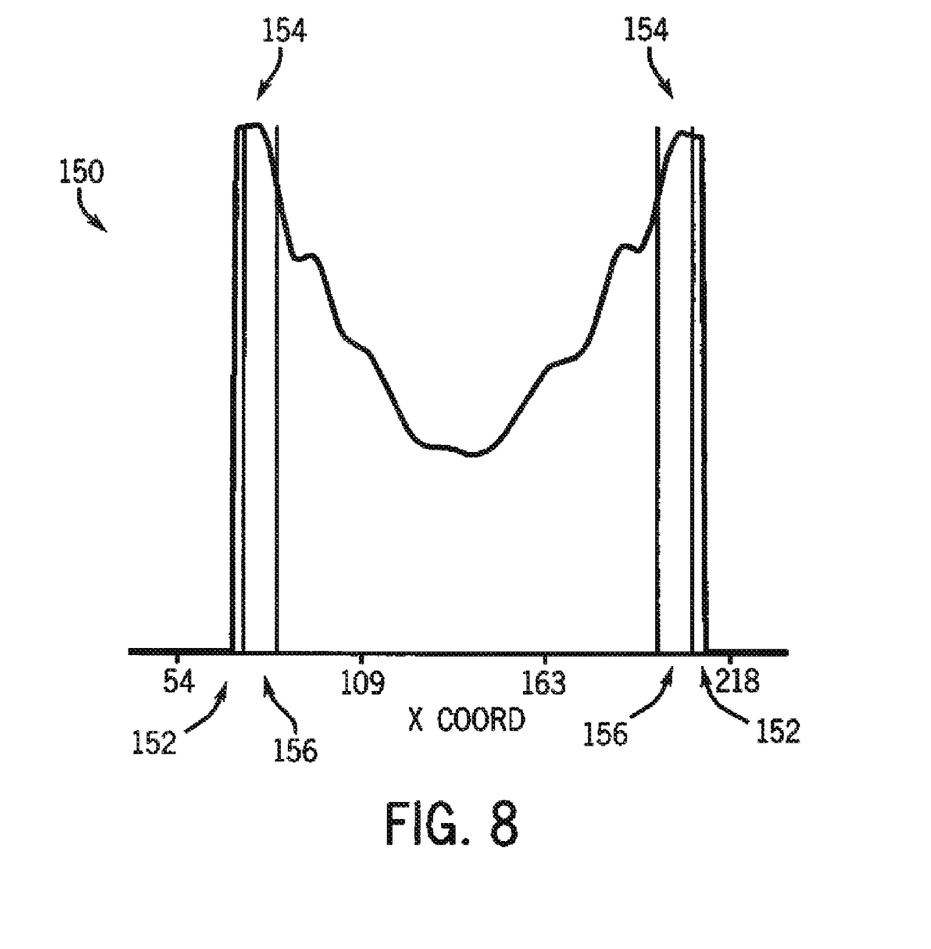
FIG. 8 is a soft tissue composition profile formed in accordance with various embodiments.

A soft tissue composition profile 150 as shown in FIG. 8 may be generated from the soft tissue or tissue thickness information and identifies the soft tissue (e.g., fat) thickness or mass across one or more lines of the scanned body, for example, one or more scan lines within the android region 110. The soft tissue composition profile 150 illustrates that the thickness or mass is generally greater at the borders of the body identified by the lines 152 than in the middle of the body. The soft tissue composition profile 150 shows the change in thickness or mass of the soft tissue based on, for example, the change in attenuation of an x-ray signal through that portion of the body. It should be noted that the values for the soft tissue composition profile 150 in some embodiments is an average composition over the vertically integrated scan lines for all horizontal positions, for example, over the entire body or one of the sections. Accordingly, the soft tissue composition profile 150 is a composition distribution in the horizontal direction, namely from right to left or left to right across the entire body. In some embodiments, the soft tissue composition profile 150 is generated only for one section, for example, the superior section 126.

The subcutaneous fat mass or area is then determined at 92 based on the soft tissue composition profile 150, for example, determined for the section 126. It should be noted that in various embodiments the subcutaneous fat mass or area is determined differently for each of the sections 124 and 126. Specifically, as can be seen from FIG. 8, the distribution of the soft tissue composition profile 150 includes two peaks 154 at both ends that represent the subcutaneous fat layer. The subcutaneous fat layer thickness is then measured by thresholding the soft tissue composition profile 150. For example, for each side, the peak is specifically identified. The minimum of the profile is then determined. The threshold is then set at a predetermined value from the minimum to the maximum (peak), for example, set at the point of maximum derivative, as illustrated by the lines 156. Accordingly, the initial calculated thickness of the subcutaneous fat mass or area is the distance from the threshold to the end of the profile (between lines 156 and 152 in FIG. 8), which is then multiplied by an empirically derived constant. The constant may be derived based on empirical studies or simulations. This multiplication operation is performed because the threshold value will not necessarily correspond exactly to the inner extent of the subcutaneous fat region, because the threshold value is the edge of a circular region. In the various embodiments, the average of the final calculated thickness for the left and right side of the body is used for the estimated subcutaneous thickness. Thus, virtual calipers defined by the threshold values are used to define the thickness of the subcutaneous fat at the perimeter of the android region.

Figure 9:
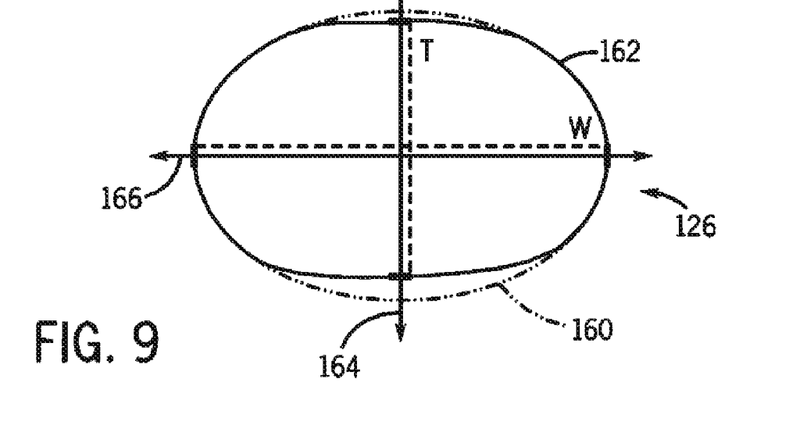
FIG. 9 is a diagram illustrating the use of an ellipse in an elliptical model to approximate the cross-section of an imaged section in accordance with various embodiments.

Thereafter, for the superior section 126, the cross-section of the android region 110 can be approximated as an ellipse 160 as shown in FIG. 9. In particular, the cross-section of the anterior section 126 of the android region 110 does not necessarily have a smooth, consistent and/or regular cross-section. For example, the cross-section of the anterior section 126 may have a boundary 162 that is irregular or non-elliptical. In accordance with various embodiments, the height of the ellipse 160 is determined from the peak thickness of the soft tissue image. In various embodiments, using the soft tissue information from the dual-energy x-ray scan, or the soft tissue composition profile 150, a tissue thickness along one or more scan lines may be determined. For example, using the soft tissue information from the dual-energy x-ray scan, a peak tissue thickness of the DXA soft tissue along one or more scan lines may be determined. The peak tissue thickness then defines a distance across the imaged body, for example, from an anterior to a posterior of the body, which is used as the length of the minor axis (T) 164 of the ellipse 160.

The width of the DXA image at the anterior section 126 (e.g., at a middle or average portion thereof) defines the length of the major axis (W) 166 of the ellipse 160. Using a pixel measuring method, the width may be determined as the distance from one side of the imaged body to the other side using a pixel count (as each pixel in the full body dual-energy image has a known size in the vertical and horizontal direction). The pixel count may start, for example, from a left side boundary of the imaged body and continue to a right side boundary of the imaged body.

The subcutaneous adipose tissue or subcutaneous fat mass is determined as the subcutaneous adipose tissue area of the section, for example, the superior section 126, which is calculated by taking the subcutaneous adipose tissue thickness determined at 90 and multiplying that value by the circumference of the ellipse 160.

It should be noted that the perimeter or circumference of the ellipse 160 may be determined using mathematical calculations as are known that calculate the perimeter or circumference either exactly or using approximations. Specifically, the perimeter or circumference of the ellipse 160 may be calculated as follows (and as is known): $4aE(\epsilon)$, where the function E is a complete elliptic integral of the second kind. In some embodiments, the perimeter or circumference may be calculated as follows: (4a)*integral (from 0 to Pi/2 of sqrt $\{(1-k^2 (\sin(theta))^2\} d(theta)$, where $k=\{sqrt(a^2-b^2)\}/a$ and a and b are the axes 166 and 164, respectively.

The perimeter or circumference may be also be approximated as the perimeter of the ellipse as follows: $2(Pi)sqrt\{(a^2+b^2)/2\}$, where a and b are the axes 166 and 164, respectively. It should be noted that any method known in the art may be used to calculate the perimeter or circumference of the ellipse 160.

Having determined the subcutaneous adipose tissue area of the superior section, and continuing with the example above, the subcutaneous adipose tissue area of the inferior section 124 is determined in a different manner. In particular, in various embodiments, the subcutaneous adipose tissue area of the inferior section 124 is determined using the ellipse 160. This section's fat mass is determined by using the fat thickness at the threshold point multiplied by half the ellipse 160 width w divided by 2, however, the anterior half of the ellipse's 160 thickness is used from the thickness value of the superior section 126, and the posterior half of the ellipse's 160 thickness is calculated based on the tissue information for the inferior section 124 using the method described above. Thus, the anterior half of the inferior section 124 is closely modeled by copying the elliptical parameters from the superior section 126. The various embodiments implement this method as the anterior of the abdomen is quite uniform from the superior side to the inferior side of the android region, while the posterior of the abdomen is not.

It should be noted that different methods may be used to calculate the subcutaneous adipose tissue area of the different sections and are not limited to the methods described above. For example, different profiles or models may be used for each of the sections.

Referring again to the method 80 of FIG. 3, the visceral fat mass is then determined at 94 based on the determined subcutaneous fat thickness and total fat thickness (from the dual-energy imaging scan). In particular, the total subcutaneous fat volume is calculated by adding up the elliptical cross sections for the sections, for example, the inferior section 124 and superior section 126. The subcutaneous volume is the area times the height of the region of interest.

Figure 10:
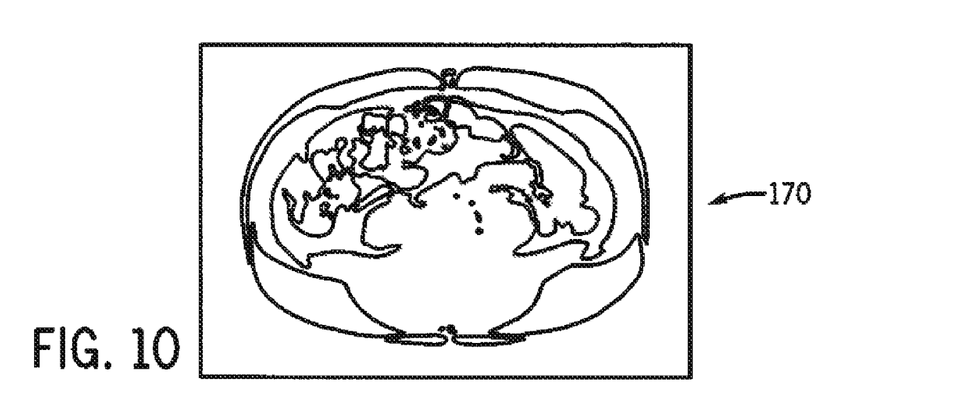
FIG. 10 is a cross-sectional image illustrating total fat in an abdomen region.
Figure 11:
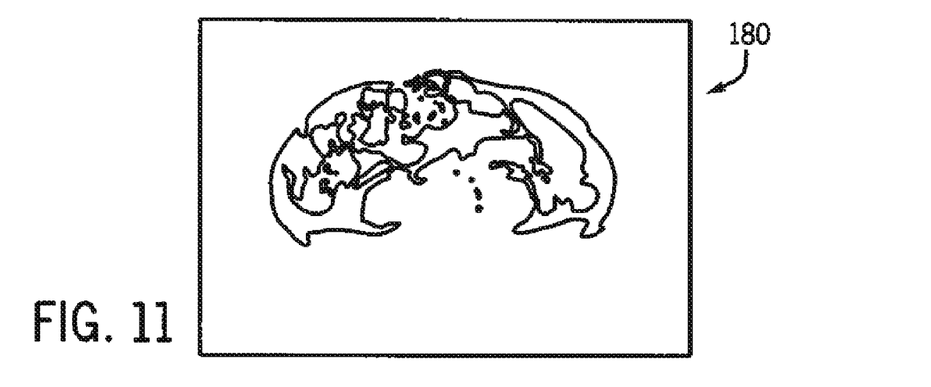
FIG. 11 is a cross-sectional image illustrating visceral fat in the abdomen after removal of the subcutaneous fat from the image.

The total visceral fat mass is then determined at 96. Specifically, the visceral fat mass is the total fat in the abdomen, which may be determined from the tissue information from the DXA scan, and as shown in the image 170 of FIG. 10, minus the subcutaneous fat calculated as described above. The resulting visceral adipose tissue mass or visceral fat mass is represented by the image 180 in FIG. 11, which is the total fat mass less the calculated subcutaneous fat mass. A total visceral fat mass value 190 and/or a total subcutaneous fat mass value may be displayed, for example, adjacent the dual-energy x-ray image at 98 and as shown in FIG. 1. It should be noted that individual visceral fat values and/or subcutaneous fat values for each section may also be separately displayed.

Thus, various embodiments of the invention use DXA technology to measure the soft tissue composition in a planar image of the abdomen, and then measure the subcutaneous fat thickness on the sides of the body to calculate the subcutaneous fat mass. The subcutaneous fat mass is then subtracted from the total abdominal fat mass to yield the visceral fat mass. The DXA image of the abdomen is a planar image (two-dimensional image) that does not specifically identify where the fat lies in the vertical plane. The DXA image does measure total abdominal fat. The thickness of the subcutaneous fat layer, which surrounds the midriff, is measured using the soft tissue (fat) composition profile. As the thickness is known, then the volume of subcutaneous fat can be determined or estimated by assuming an elliptical cross-section for the subcutaneous fat. The value of the volume of the subcutaneous fat is then subtracted from the total fat in the abdomen to yield the visceral fat mass.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for determining visceral fat of a body, the method comprising:
   acquiring dual-energy two-dimensional (2D) scan information from a dual-energy x-ray scan of a body;
   generating a dual-energy image of the body using the 2D scan information;
   identifying a region of interest using the dual-energy image;
   wherein the region of interest is separated into a superior area and an inferior area;
   determining a subcutaneous fat mass for each of the superior area and the inferior area of the region of interest; and
   determining a visceral fat mass for the region of interest based on the determined subcutaneous fat mass for each of the superior area and the inferior area;
   wherein each of the superior area and the inferior area is separated into an anterior section and a posterior section.

2. A method in accordance with claim 1 further comprising estimating the subcutaneous fat mass for each of the superior area and the inferior area using different models.

3. A method in accordance with claim 2 further comprising using an elliptical model for a cross-section of the superior area to determine the subcutaneous fat mass.

4. A method in accordance with claim 3 wherein the elliptical model uses tissue information from the anterior section and the posterior section of the superior area to determine the subcutaneous fat mass.

5. A method in accordance with claim 3 wherein the elliptical model uses tissue information from the anterior section of the inferior area to determine the subcutaneous fat mass.

6. A method in accordance with claim 3 wherein a height of an ellipse of the elliptical model is determined from a peak tissue thickness for the superior area and a width of the ellipse is determined from a width of the dual x-ray image at the superior area.

7. A method in accordance with claim 2 further comprising using a non-elliptical model for a cross-section of the inferior area to determine the subcutaneous fat mass.

8. A method in accordance with claim 7 wherein the non-elliptical model uses tissue information from the posterior section of the inferior area to determine the subcutaneous fat mass.

9. A method in accordance with claim 1 wherein the region of interest comprises an android region of the body.

10. A method in accordance with claim 9 further comprising identifying the android region using bone information from the dual-energy image.

11. A method in accordance with claim 10 further comprising identifying the android region using a top of an iliac crest bone and wherein the android region is defined as a region between the top of the iliac crest and a distance that is defined by twenty percent of a distance from the top of the iliac crest to a base of a skull.

12. A method in accordance with claim 1 further comprising generating a soft tissue composition profile for each of the superior area and the inferior area to use in determining the subcutaneous fat mass for the superior area and the inferior area.

13. A method in accordance with claim 12 further comprising applying thresholding to each of the soft tissue composition profiles to define an area of the profiles for determining the subcutaneous fat mass for the superior area and the inferior area.

14. A method in accordance with claim 1 wherein the visceral fat mass is total fat mass minus subcutaneous fat mass in each of a superior anterior region, a superior posterior region, an inferior anterior region, and an inferior posterior region.

* * * * *